United States Patent
Zadeh

(10) Patent No.: US 10,402,962 B2
(45) Date of Patent: Sep. 3, 2019

(54) AUTOMATED BEAD DETECTION AND DETECTION TRAINING

(71) Applicant: COGNEX CORPORATION, Natick, MA (US)

(72) Inventor: Ali Zadeh, Hopkinton, MA (US)

(73) Assignee: COGNEX CORPORATION, Natick, MA (US)

(*) Notice: Subject to any disclaimer, the term of this patent is extended or adjusted under 35 U.S.C. 154(b) by 0 days.

(21) Appl. No.: 15/656,747

(22) Filed: Jul. 21, 2017

(65) Prior Publication Data

US 2019/0026880 A1 Jan. 24, 2019

(51) Int. Cl.
G06T 7/00 (2017.01)
G01B 11/02 (2006.01)
G01B 11/24 (2006.01)
G01N 21/25 (2006.01)

(52) U.S. Cl.
CPC .......... *G06T 7/001* (2013.01); *G01B 11/022* (2013.01); *G01B 11/24* (2013.01); *G01N 21/251* (2013.01); *G06T 2207/20081* (2013.01); *G06T 2207/20104* (2013.01); *G06T 2207/30164* (2013.01)

(58) Field of Classification Search
CPC ........... G06T 7/001; G06T 2207/20104; G06T 2207/20081; G06T 2207/30164; G01B 11/24; G01B 11/022; G01N 21/251
See application file for complete search history.

(56) References Cited

U.S. PATENT DOCUMENTS

| | | | | |
|---|---|---|---|---|
| 4,704,603 A | * | 11/1987 | Edwards | G01V 8/20 250/223 R |
| 2002/0151043 A1 | * | 10/2002 | Gordon | B01L 3/5027 435/287.2 |
| 2010/0003904 A1 | * | 1/2010 | Duescher | B24B 37/14 451/259 |

OTHER PUBLICATIONS

Omron Corporation, Vision Sensor Software for Glue Bead Inspection, Jan. 5, 2010, https://www.automationmag.com/products/machine-vision-inspection/317-vision-sensor-software-for-glue-bead-inspection. (Year: 2010).*
Coherix, Predator3D(TM)—3D Bead Inspection for Sealing Applications, Product Information, Copyright 2015 Coherix.
GVi Ventures, RTV Bead Inspect, Product Information, http://gviventures.com/applications/rtv-bead-inspect/, Copyright 2013 GVi Ventures.
Omron Corporation, FZ3-UGI / UGIH Vision Sensor Software for Glue Bead Inspection/Features, Product Information, http://www.omron-ap.com/products/family/2631/, Last Update: Apr. 4, 2013.
Vision Systems Design, Matrox Design Assistant 2.3 Smart Camera Software Offers Bead Inspection Tool and Simplified Fixturing, http://www.vision-systems.com/articles/2010/09/matrox-design-assistant-2-3-.html, Sep. 3, 2010.

* cited by examiner

*Primary Examiner* — Yon J Couso
(74) *Attorney, Agent, or Firm* — Quarles & Brady LLP

(57) ABSTRACT

A system and method for training a bead detection system can include identifying a starting region on a bead based on a starting indicator. The bead can be analyzed at the starting region to identify bead characteristics. The bead can then be analyzed away from the starting region, based on the identified bead characteristics, to identify a bead profile for use during non-training bead inspection.

20 Claims, 13 Drawing Sheets

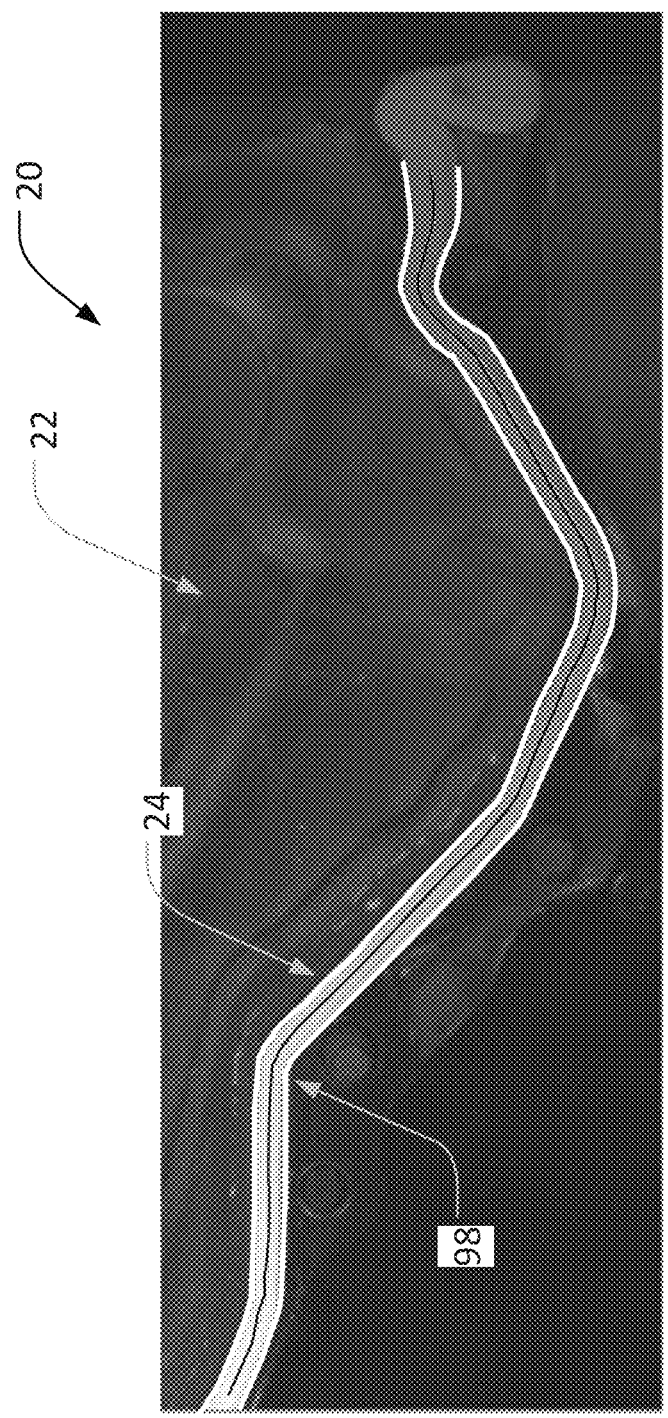

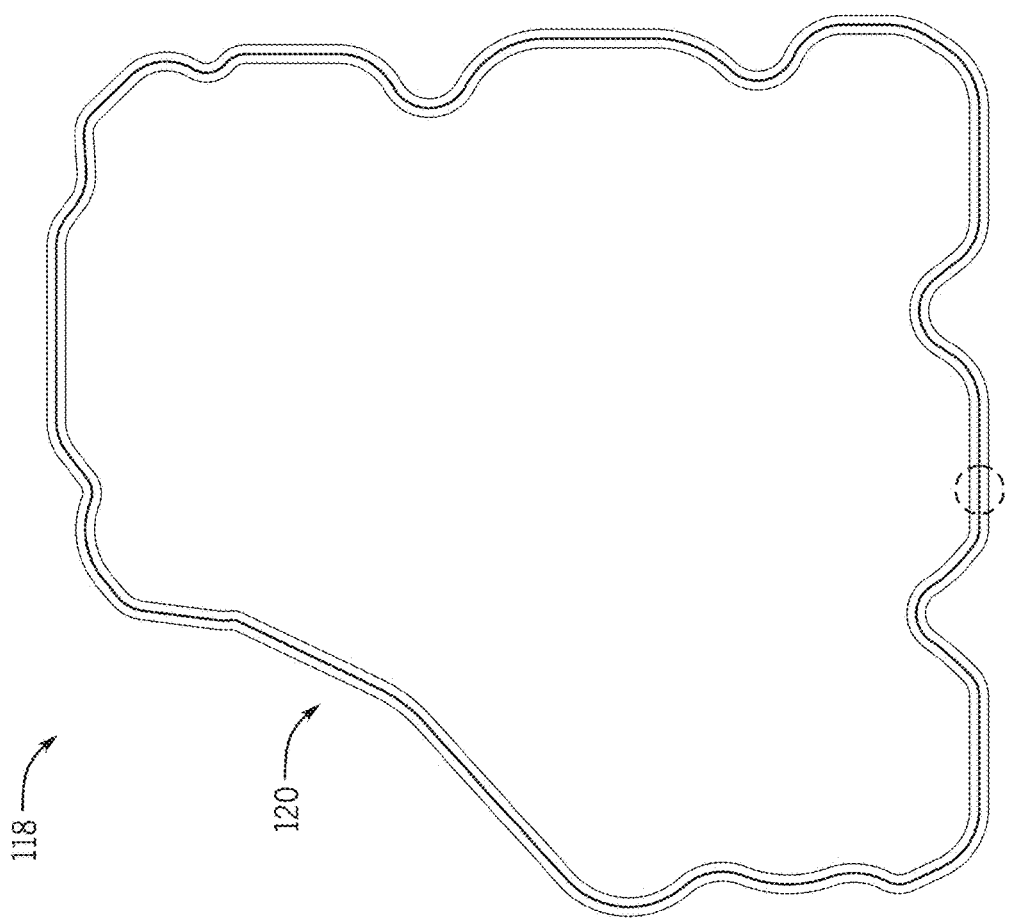

AUTOMATED BEAD DETECTION AND DETECTION TRAINING

CROSS-REFERENCE TO RELATED APPLICATIONS

Not applicable.

STATEMENT REGARDING FEDERALLY SPONSORED RESEARCH OR DEVELOPMENT

Not applicable.

FIELD OF THE INVENTION

The present invention relates to detecting and evaluating beads that have been applied to structures.

BACKGROUND OF THE INVENTION

In many contexts, it may be useful to deposit (or otherwise apply) beads of extruded material onto different substrates (e.g., structures of industrial parts). For example, in automotive, medical device and consumer electronic product assemblies, and other industrial and commercial applications it may be useful to apply adhesive or other sealant material to gaskets or other areas for attachment of different parts, and so on.

For different reasons, it can be important for a particular bead to trace a particular path with relatively high precision (e.g., with less than a predetermined deviation with regard to the desired path). It can also be important for a particular bead to exhibit different properties to within a desired degree of accuracy. For example, in different applications, it may be important for beads to exhibit a relatively uniform (or otherwise specified) bead thickness, bead continuity, and so on.

SUMMARY OF THE INVENTION

Technologies are described for identifying beads on structures, and in particular for identifying beads as part of a training operation for subsequent automated bead detection and inspection.

Some embodiments of the invention provide a computer-implemented training method for a bead detection system, for use with a training image that includes a representation of a bead on a substrate. An input can be received designating a starting indicator that corresponds to a discrete portion of the bead on the training image. The training image can be analyzed at the starting indicator to identify one or more characteristics of the bead. Based on the one or more characteristics of the bead, one or more portions of the bead that are spaced apart from the starting indicator can be analyzed to identify a candidate bead profile. The candidate bead profile can be provided to an inspection module for subsequent inspection of beads in non-training images.

Some embodiments of the invention provide a computer-implemented training method for a bead detection system, for use with a training image that includes a representation of a bead on a structure. A starting region can be identified on the bead on the training image based upon a user-designated starting indicator. The bead can be analyzed within the starting region to identify one or more characteristics of the bead. The bead can be analyzed outside of the starting region, based on first analysis parameters and the one or more characteristics of the bead, to identify a first candidate bead profile. The bead can be analyzed outside of the starting indicator, based on the one or more characteristics of the bead and second analysis parameters that are different from the first analysis parameters, to identify a second candidate bead profile. An inspection bead profile can be determined based on at least one of the first candidate bead profile and the second candidate bead profile. The inspection bead profile can be provided to an inspection module for subsequent inspection of beads in non-training images.

Some embodiments of the invention provide a bead recognition training system. An imaging device can be configured to capture a training image of a bead. An analysis module can be configured to receive the training image; to receive a user input that provides a starting indicator designating a discrete portion of the bead on the training image, with substantially all of the bead on the training image being located outside of the discrete portion; to analyze the bead within the discrete portion of the bead to identify one or more characteristics of the bead; to analyze the bead outside of the discrete portion of the bead, based on the identified one or more characteristics of the bead, to determine one or more candidate bead profiles; and to provide at least one of the candidate bead profiles to an inspection module for subsequent inspection of beads in non-training images.

To the accomplishment of the foregoing and related ends, embodiments of the invention, then, can include the features hereinafter fully described. The following description and the annexed drawings set forth in detail certain example aspects of the invention. However, these aspects are indicative of but a few of the various ways in which the principles of the invention can be employed. Other aspects, advantages and novel features of the invention will become apparent from the following detailed description of the invention when considered along with the drawings.

BRIEF DESCRIPTION OF THE DRAWINGS

The features and advantages of the invention are apparent from the following description taken in conjunction with the accompanying drawings in which:

FIG. 8 is a schematic view of the training image of FIG. 1, illustrating a presentation of a bead profile to a user according to an aspect of the invention;

FIG. 11 is a schematic view of a training image created based on the first and second reference images of FIGS. 9 and 10, according to an aspect of the invention;

DETAILED DESCRIPTION OF THE INVENTION

Figure 1:
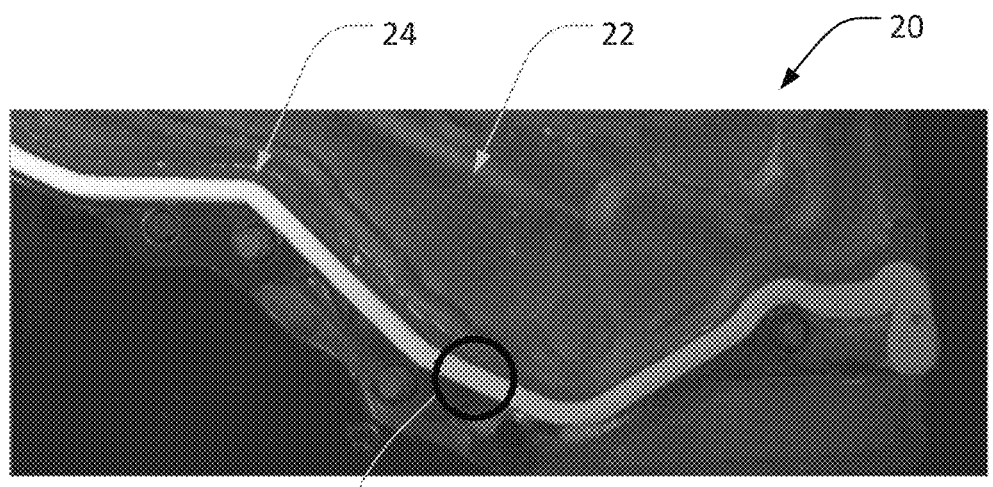
FIG. 1 is a schematic view of a training image for bead detection, with an imaged bead and an operator-initiated starting indicator according to an aspect of the invention.

In the following detailed description, reference is made to the accompanying drawings that form a part hereof. In the drawings, similar symbols typically identify similar components, unless context dictates otherwise. The example embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

In some implementations, aspects of the invention, including computerized implementations of methods according to the invention, can be implemented as a system, method, apparatus, or article of manufacture using standard programming and/or engineering techniques to produce software, firmware, hardware, or any combination thereof to control a computer or processor based device to implement aspects detailed herein. The term "article of manufacture" as used herein is intended to encompass a computer program accessible from any computer-readable device, carrier (e.g., non-transitory signals), or media (e.g., non-transitory media). For example, computer-readable media can include but are not limited to magnetic storage devices (e.g., hard disk, floppy disk, magnetic strips, and so on), optical disks (e.g., compact disk (CD), digital versatile disk (DVD), and so on), smart cards, and flash memory devices (e.g., card, stick). Additionally it should be appreciated that a carrier wave can be employed to carry computer-readable electronic data such as those used in transmitting and receiving electronic mail or in accessing a network such as the Internet or a local area network (LAN). Of course, those skilled in the art will recognize many modifications may be made to these configurations without departing from the scope or spirit of the claimed subject matter.

Embodiments of the invention can be implemented as systems and/or methods, including computer-implemented methods. Some embodiments of the invention can include (or utilize) a device such as an automation device, a special purpose or general purpose computer including various computer hardware, software, firmware, and so on, consistent with the discussion below.

As used herein, unless otherwise specified or limited, "at least one of A, B, and C," and similar other phrases, are meant to indicate A, or B, or C, or any combination of A, B, and/or C. As such, this phrase, and similar other phrases can include single or multiple instances of A, B, and/or C, and, in the case that any of A, B, and/or C indicates a category of elements, single or multiple instances of any of the elements of the category (or categories).

Also as used herein, unless otherwise specified or limited, the terms "component," "system," "module," and the like are intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a computer and the computer can be a component. One or more components (or system, module, and so on) may reside within a process and/or thread of execution, may be localized on one computer, distributed between two or more computers or processors, and/or included within another component (or system, module, and so on).

Also as used herein, unless otherwise specified or limited, "irregular" and variations thereupon are generally used to refer to portions of beads in which edges of the bead are not formed as expected, vary from surrounding portions of the bead (e.g., in total width, contrast, etc.), or exhibit one or more unclear edges (e.g., due to proximity to a hole in or edge of an object to which the bead is applied).

Also as used herein, unless otherwise specified or limited, "light-on-dark" refers to features of interest that are generally imaged as lighter than the surrounding background. Similarly, "dark-on-light" refers to features of interest that are generally imaged as darker than the surrounding background.

As also discussed above, it may be useful to inspect beads that have been applied to structures for different characteristics. However, conventional approaches to bead inspection can be inefficient and/or unreliable. For example, in some cases, beads are visually inspected by workers once deposited on a particular substrate (e.g., a particular industrial part). While expert workers can identify many bead deficiencies, this type of visual inspection can be slow and prone to errors. Further, training of workers to ensure appropriate inspection techniques and execution can be time-consuming and expensive.

As another example, conventional automated inspection approaches can usefully improve on the time required for visual inspection of beads by workers. However, substantial investment of time to appropriately train automated systems can sometimes be required in order to ensure appropriate inspection accuracy. Further, training of conventional automated inspection systems may often rely on visual inspection and/or manual input and analysis of parameters by workers. For example, in some conventional approaches, bead inspection tools are configured to be trained (or otherwise operate) by accepting a user-defined coarse path (e.g., as a list of points) for a reference bead, and then automatically placing search boxes on the path to form a template. As the training progresses, the size and spacing of these search boxes can be manually modified to change the sampling resolution or other parameters. Likewise, parameters including allowable bead width, offset, gap and overall acceptance criteria can also be adjusted to meet specific inspection requirements. For these and other approaches, accordingly, the task of training a bead path for inspection is conventionally allocated to skilled machine vision engineers, thereby further increasing the required investment of time and other resources. Further, even for expert workers, identification of appropriate bead characteristics and analysis parameters can sometimes rely mainly on trial-and-error and/or personal intuition, thereby further increasing the possibility of lengthy, inefficient, and/or ineffective implementation.

Different embodiments of the invention can address these and other issues. For example, in some embodiments, the invention can generally reduce the time needed to train a vision system for reliably inspecting beads (e.g., beads of glue or sealant) as well as the required input from workers, while also allowing for reliable training of the vision system based on input even from non-expert users.

In some embodiments, a training image can be received at a bead inspection system, and a worker can provide a starting indicator for analysis of the bead on the training image. For example, a worker can simply provide an electronically implemented marker (e.g., a circle) on the training image to indicate a portion of the bead with relatively representative characteristics (e.g., width, color, contrast, and so on). The bead inspection system can then automatically analyze the bead, starting at the starting indicator, in order to identify bead properties, and, subsequently, one or more candidates for a profile of the bead along the substrate. As appropriate, the user can then select one or more of the candidate profiles, as well as modify a selected bead profile (or other parameters). Finally, an appropriate (e.g., user-selected and -modified) candidate profile can be provided to a bead inspection module (e.g., as part of a large bead inspection system) for identification and evaluation of beads on non-training images, based on the bead profile and properties that were identified based on the training image.

In some embodiments, as partially expressed in the example above, a useful aspect of the invention includes the ability to identify bead profiles and other relevant parameters during system training with relatively minimal input from users. In some embodiments, this aspect may correspond to a user initially providing only a starting indicator that encompasses a discrete and relatively small portion of a relevant bead on a training image (e.g., such that the majority of the bead is outside of the starting indicator). For example, as illustrated in FIG. 1, a bead inspection system can be configured to receive a training image 20, that can include a representation of a substrate structure 22 (e.g., an automotive part) and a bead 24 that has been applied to the structure 22. Based upon a relatively quick and potentially non-expert analysis of the training image 20, a user can electronically provide a starting indicator 26 on the image to identify a starting region on the bead 24 for training analysis. As also described below, the bead inspection system can then undertake an analysis of the training image 20 and the bead 24, in order to train itself (or another system) to identify and analyze similar beads in subsequent non-training images.

In different embodiments, a user can provide a starting indicator in different ways and with different characteristics. In the embodiment illustrated, for example, the staring indicator 26 is configured to be a simple circle, which is configured to be somewhat larger in diameter than the expected bead width (e.g., 3 or 4 times the expected bead width) can be simply placed (e.g., by mouse-click or touch-screen interaction) on a portion of the bead 24 that is relatively characteristic of the bead 24 as a whole. In other embodiments, a starting indicator can exhibit other indicator shapes or characteristics, and can be placed in other ways, including automatically or semi-automatically.

Generally, once a starting indicator has been appropriately implemented (e.g., appropriately placed on a training image) and other inspection parameters have determined (e.g., based on default settings not entered by the relevant user), the bead inspection system can proceed with analysis of the relevant bead in order to identify relevant bead characteristics. In this regard, for example, using the starting indicator to identify a region of interest, the bead inspection system can analyze a portion of the bead (e.g., as contained within a starting indicator) using a variety of known machine-vision techniques, in order to identify parameters at the starting indicator including bead color, bead width, initial bead direction, and so on.

Figure 2:
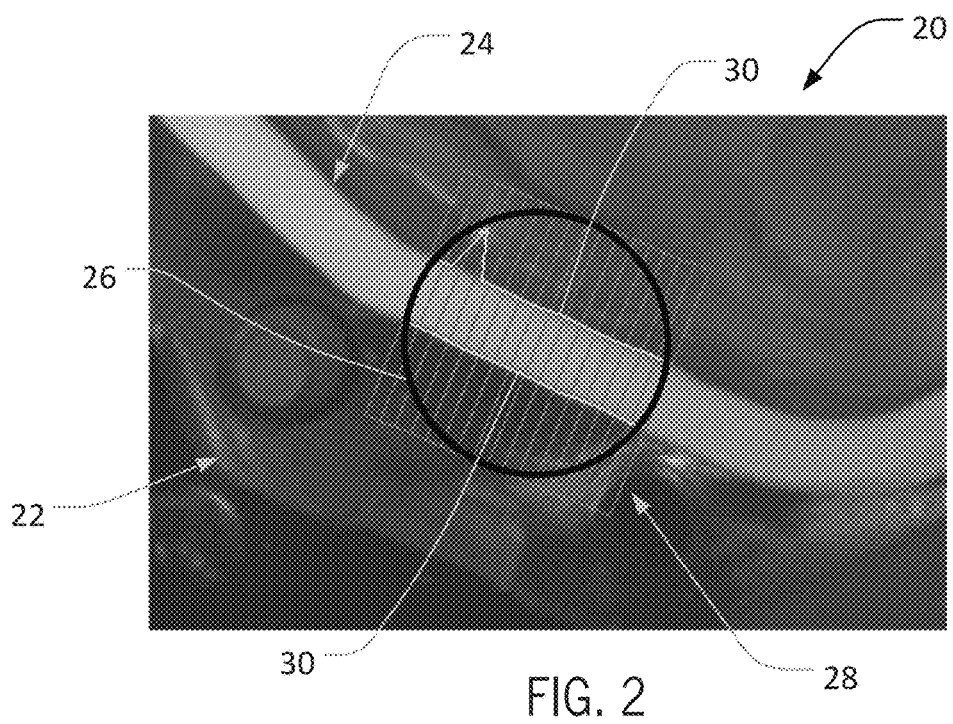
FIG. 2 is a partial schematic of the training image of FIG. 1, illustrating an initial analysis of the imaged bead according to an aspect of the invention.

As illustrated in FIG. 2, for example, based on the placement of the starting indicator 26 a set of calipers 28 can be virtually imposed over the bead 24. Using any of a number of known techniques, the calipers 28 can then be used in order to identify the relevant color, width, and direction of the bead 24 at the starting indicator 26, and/or various other properties. In some embodiments, as also noted above, analysis with the calipers 28 can proceed based on default analysis parameters (e.g., default caliper width, offset, and so on), so that machine-vision expertise may not be required from the user that initiates the analysis.

In some embodiments, the calipers 28 can be rotated by predetermined intervals (e.g., 22.5 degrees) in order to analyze the bead 24 from a number of relative angles. This can be useful, for example, in combination with edge-finding and line-fitting algorithms, in order to identify best-candidate edge pairs for the bead 24 within the starting indicator 26 and thereby identify a best-candidate outline and direction for the bead 24 at the starting indicator 26. As illustrated in FIG. 2, this can usefully result in a relatively high-confidence identification of edges 30 of the bead 24 at the starting indicator 26, as well as a direction of the bead 24 at the starting indicator 26 (not specifically illustrated in FIG. 2).

In different embodiments, different properties of the bead 24 at the starting indicator 26, as well as other relevant parameters can also (or alternatively) be identified based upon analysis of the bead 24 at the starting indicator 26. For example, in some embodiments, analysis using the calipers 28, as indicated in FIG. 2, can result in identification of not only bead color, bead width, and initial bead direction, but also a minimum contrast for the bead, an appropriate extension of calipers beyond the expected bead for subsequent analysis (e.g., an appropriate half scan width for the calipers), and other image analysis parameters (e.g., half widths for Gaussian or other filters, and so on).

In some embodiments, analysis of a bead at a starting indicator can proceed based on a known (or expected) characteristic of a bead. For example, if it is known (or expected) that the bead 24 will be imaged as a light-on-dark bead, analysis of the bead 24 using the calipers 28 can proceed accordingly within the starting indicator 26. In this regard, for example, a default or user-provided setting can appropriately orient analysis of the bead to the relevant bead color. In other embodiments, however, analysis of a bead at a starting indicator can allow for alternative possibilities (e.g., with regard to bead color or other characteristics). For example, if the expected color of the bead 24 is not known (or in other circumstances), analysis of the bead 24 using the calipers 28 can be executed for both light-on-dark and dark-on-light beads, and an actual (or apparent) bead color can be determined accordingly.

In some implementations, once a starting indicator has been identified (or at other times), a user can adjust different parameters in the bead inspection system, in order to assist the system in appropriately identifying the relevant bead. For example, as appropriate, a user can adjust parameters such as a bead color scheme (e.g., light-on-dark or dark-on-light beads), bead contrast level (e.g., an expected level of contrast between the bead and the relevant surrounding or background structure), bead width, and other analysis parameters (e.g., how far outside of bead a set of calipers should extend), and so on. In some implementations, in contrast, a user can rely on default settings for these or other parameters, and can initially provide input relating mainly (e.g., only) to the starting indicator.

Once appropriate characteristics of a bead have been identified based on analysis at a starting indicator, the bead inspection system can then proceed with further analysis of the bead at locations spaced apart from (e.g., outside of) the starting indicator. In some embodiments, this can include initially stepping along the bead in one direction, starting at the starting indicator and analyzing successive adjacent regions of the bead in turn. For example, as illustrated in FIG. 2, analysis of the bead 24 within the starting indicator 26 can result in identification of a relatively high-confidence identification of the edges 30 of the bead 24 within the starting indicator 26, as well as, correspondingly, a relatively high-confidence initial direction of the bead 24 (not expressly illustrated in FIG. 2). Based upon this initial direction, analysis of the bead 24 can then proceed, moving step by step away from the starting indicator 26 in a first direction (e.g., generally to the right, from the perspective of FIG. 2).

In some embodiments, analysis of a bead away from a starting indicator can proceed somewhat similarly to analysis of the bead within the starting indicator, albeit with the benefit of relevant bead characteristics (e.g., color, contrast, and so on) having been already determined for the bead based on the analysis at the starting indicator. For example, based on an initial direction for the bead 24 (e.g., as determined based on analysis at the starting indicator 26, as illustrated in FIG. 2), successive groups of calipers can be used to analyze discrete portions of the bead 24, with each group of calipers being used to identify local bead edges and bead direction (and/or other parameters) in order to guide placement of a subsequent group of calipers.

Figure 3:
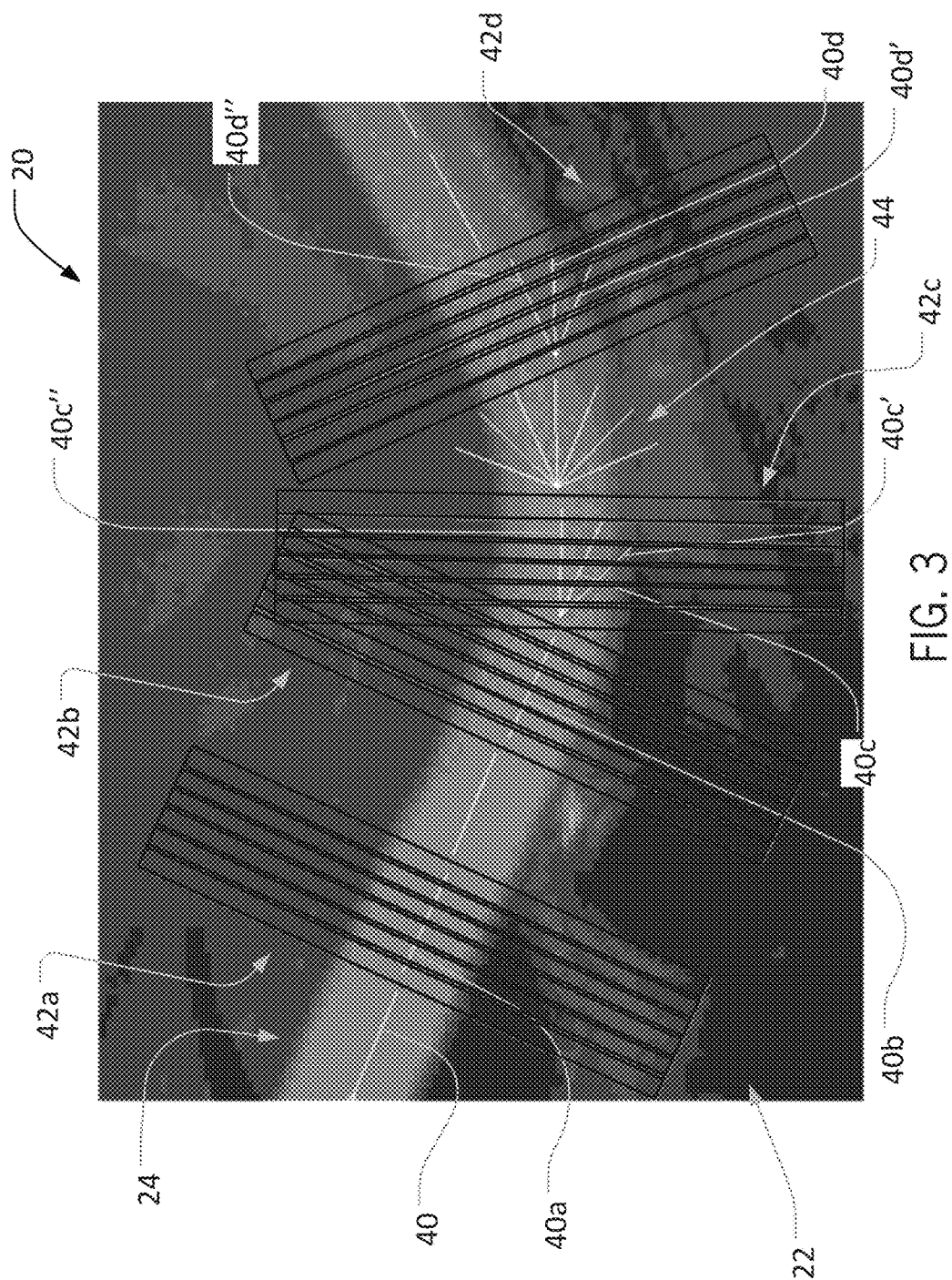
FIG. 3 is a partial schematic of the training image of FIG. 1, illustrating a succession of analysis operations on the imaged bead to identify a bead path according to an aspect of the invention.

In this way, for example, a set of discrete points (or lines) identifying a bead path for the bead 24 can be identified. For example, as illustrated in FIG. 3, based upon a previously determined bead direction 40, a caliper group 42a can be placed in order to analyze a discrete portion of the bead 24. Based upon analysis with the caliper group 42a, a subsequent local bead direction 40a can be identified (as well as, for example local edges of the bead 24), which can be used to guide placement of a subsequent caliper group (not shown). Based upon analysis by that caliper group, a further subsequent caliper group 42b can be placed, which can result in identification of another local bead direction 40b, and so on. In this way, for example, based on an assumed local linear continuity of the bead 24 between adjacent bead regions, successive groups of calipers (or other analysis tools) can be used to identify local bead profiles (e.g., bead edges and directions) along the length of the bead 24.

In some instances, placement of a successive caliper group based on a preceding bead direction may result in a relatively low-confidence identification of a bead direction (or other bead characteristics). For example, as illustrated in FIG. 3, a group of calipers 42c placed along an extension of the bead direction 40b and oriented perpendicularly to the bead direction 40b (such caliper orientation not expressly shown) may result in relatively low-confidence identification of bead edges and direction for the bead 24. In such a case, the bead inspection system can rotate the orientation of the relevant caliper group (e.g., in regular angular intervals, with successively alternating directions) in order to identify a higher-confidence set of bead properties.

As illustrated in FIG. 3, for example, based upon a low-confidence result of caliper-based analysis along a direction 40c that is a linear extension of the direction 40b, the bead inspection system can analyze the bead 24 by rotating the caliper group 42c by 22.5 degrees (or another angular distance) clockwise and counterclockwise, alternately, from the direction 40c (e.g., to directions 40c' and 40c''). The highest-confident identification of the local characteristics of the bead 24 of these alternative-orientation analyses (e.g., the direction 40c'') can then be selected as the identified local direction for the bead 24. Correspondingly, analysis of an adjacent portion of the bead 24 (i.e., to the right in FIG. 3) can proceed with an initial assumption that the bead 24 continues along the direction 40c''.

In the example discussed above, an appropriate bead direction (i.e., the direction 40c'') was successfully identified after deviating from the direction 40c by only a single interval in the clockwise and counterclockwise directions. In other cases, additional rotational intervals (e.g., intervals successively increased by 22.5 degrees) may be necessary. In some implementations, it may be appropriate to place a limit on these successive rotational intervals, such as a limit permitting analysis of a bead in a particular region only up to 90 degrees deviation from an expected bead direction (e.g., as determined based on an adjacent, previously analyzed bead region).

In some cases, despite analysis of a bead segment along alternative expected directions (e.g., as discussed above), it may not be possible to identify bead characteristics (e.g., edge location and local bead direction) with appropriate confidence. In some implementations, accordingly, it may be possible to "skip" forward to a subsequent (e.g., adjacent) region on the bead for further analysis. As illustrated in FIG. 3, for example, based on an assumed direction 40c'', analysis of the bead 24 has been undertaken with caliper groups (not shown) at a location 44. However, despite attempted analyses with the caliper groups for a set of expected directions at the location 44 that range up to 90 degrees to either side of an extension of the direction 40c'', it may not be possible to characterize the bead 24 with appropriate confidence. Accordingly, the bead inspection system can progress (i.e., "skip") to the next adjacent portion of the bead 24. In some cases, including as illustrated in FIG. 3, such a skip may proceed based on an assumed continued linear extension of the bead along the last successfully identified bead direction (e.g., along the direction 40c'', such that a bead direction 40d is assumed for the skipped-to region). In the implementation illustrated, for example, such an analysis, using a caliper group 42d, resulted in an appropriately high confidence identification of bead characteristics with regard to a bead direction 40d''. Based on this result, the direction 40d'' can then be used to guide analysis of subsequent bead sections with subsequent caliper groups (not shown).

In some cases, it may be useful to limit the number of successive unsuccessful attempts to identify relevant bead parameters (e.g., in successive regions of a bead in a training image). This may be useful, for example, in order to help the bead inspection system to identify the end of a particular bead and/or to prevent the bead inspection system from expending excessive amounts of time on analysis using a particular set of analysis parameters (e.g., a particular set of parameters for caliper groups). Accordingly, for example, a bead inspection system can include a universal (or instance-specific) setting that specifies a maximum number of "skips," after which the system can terminate analysis (e.g., for a particular pass, or in total).

In different implementations, different numbers of permitted skips can be used. In an analysis pass for the bead 24 illustrated in FIG. 4, for example, a maximum skip number of 1 has been established. As illustrated, as analysis of the bead 24 progresses, groups of calipers 50a through 50c have been used to successfully identify bead edges 52a through 52c and bead directions 54a through 54c. However, due to different factors (e.g., poor contrast, unexpected spreading of the bead 24, and so on), analysis of the bead 24 in a region 56 immediately adjacent to the caliper group 50c failed to satisfactorily identify local characteristics for the bead 24, despite orientating relevant caliper groups over a range of potential directions 54d. In this case, with a non-zero maximum number of skips, analysis can simply progress to a next adjacent region 58.

Figure 4:
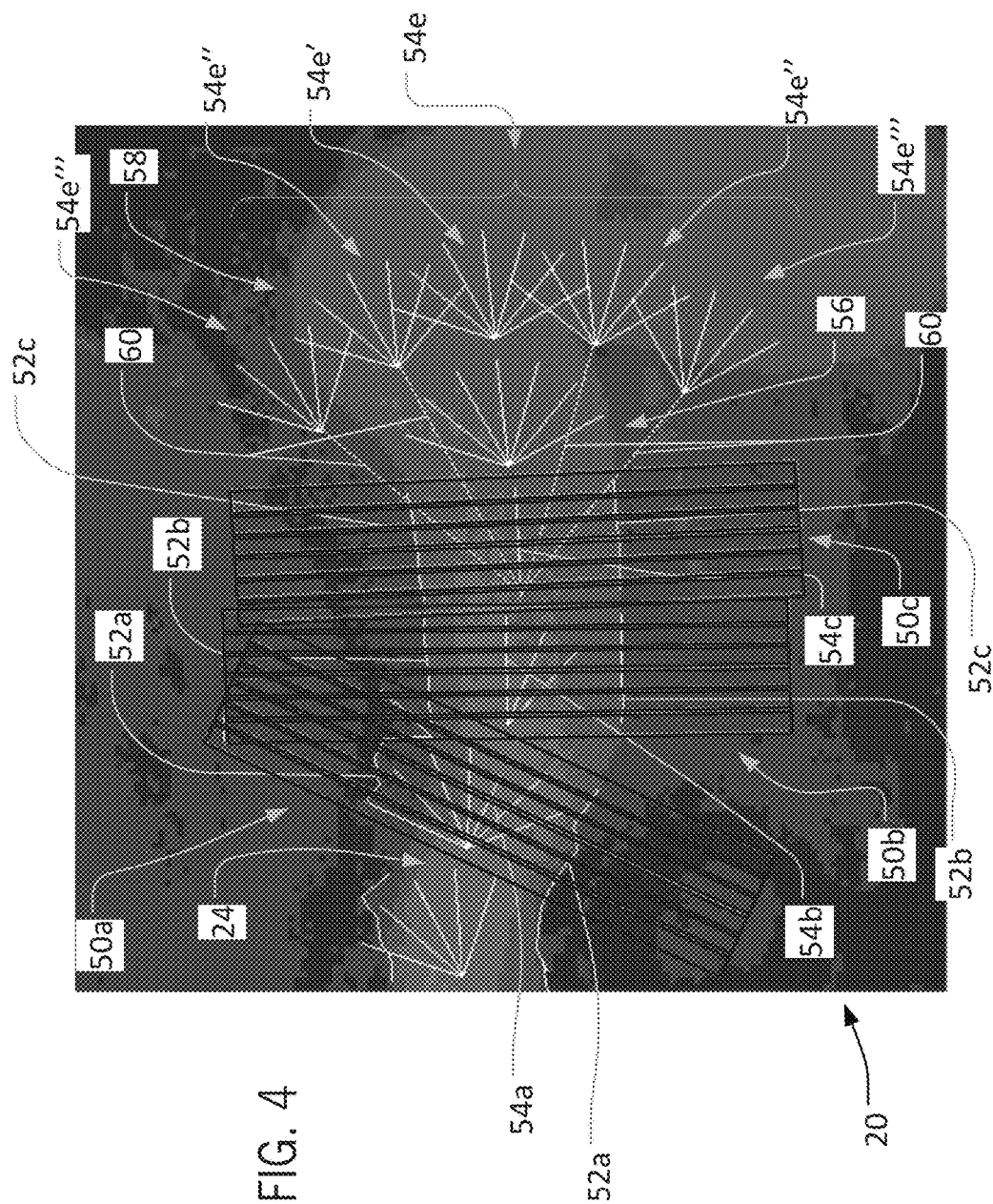
FIG. 4 is a partial schematic of the training image of FIG. 1, illustrating analysis of an irregular bead portion according to an aspect of the invention.

However, in the example presented in FIG. 4, analysis of the bead 24 at the region 58 also failed to satisfactorily identify local characteristics for the bead 24, despite orientating the caliper groups over an expanded set 54e of ranges of potential directions. At this point, because only a single skip is currently permitted according to the above-noted maximum-skip number, and because the skip has already been taken (i.e., to move from the region 56 to the region 58), the bead inspection system can cease further analysis of the bead 24 on this pass. For example, based on having exhausted the permitted skip count, the bead inspection system can consider the bead 24 to have ended, with the regions 54 and 56 not being included in the candidate profile of the bead 24 that has been constructed on this particular analysis pass.

FIG. 4 also illustrates an aspect of the invention that can help to identify local bead characteristics even in the event of substantial local deviation of a bead from a preceding bead direction. In this regard, for example, the bead inspection system can initially implement caliper (or other) analysis with an assumed extension of the last successfully identified direction (e.g., the direction 54c) and angular variations thereupon (e.g., over potential directions 54e'). However, if no appropriately high-confidence bead characteristics have been identified over the potential directions 54e', the bead inspection system can then implement caliper analysis with different assumed bead directions. For example, the bead inspection system can implement caliper analysis over bead directions that are determined based on various assumed extensions of angular deviations 60 from the last successfully identified direction 54c. In this regard, for example, caliper (or other) analysis can be implemented over successively angularly expanded groups of potential directions 54e" and 54e''' (e.g., as based around starting points identified via successive two-direction expansions of 22.5 degrees from a starting reference based on the direction 54c).

In the implementation illustrated in FIG. 4, only two evenly spaced deviations 60 to either side of the direction 54c are attempted before the bead inspection system determines a failure to successfully locally characterize the bead 24. In other implementations, other numbers of deviations and other deviation spacings (e.g., angular deviations from a reference) are possible.

Figure 5:
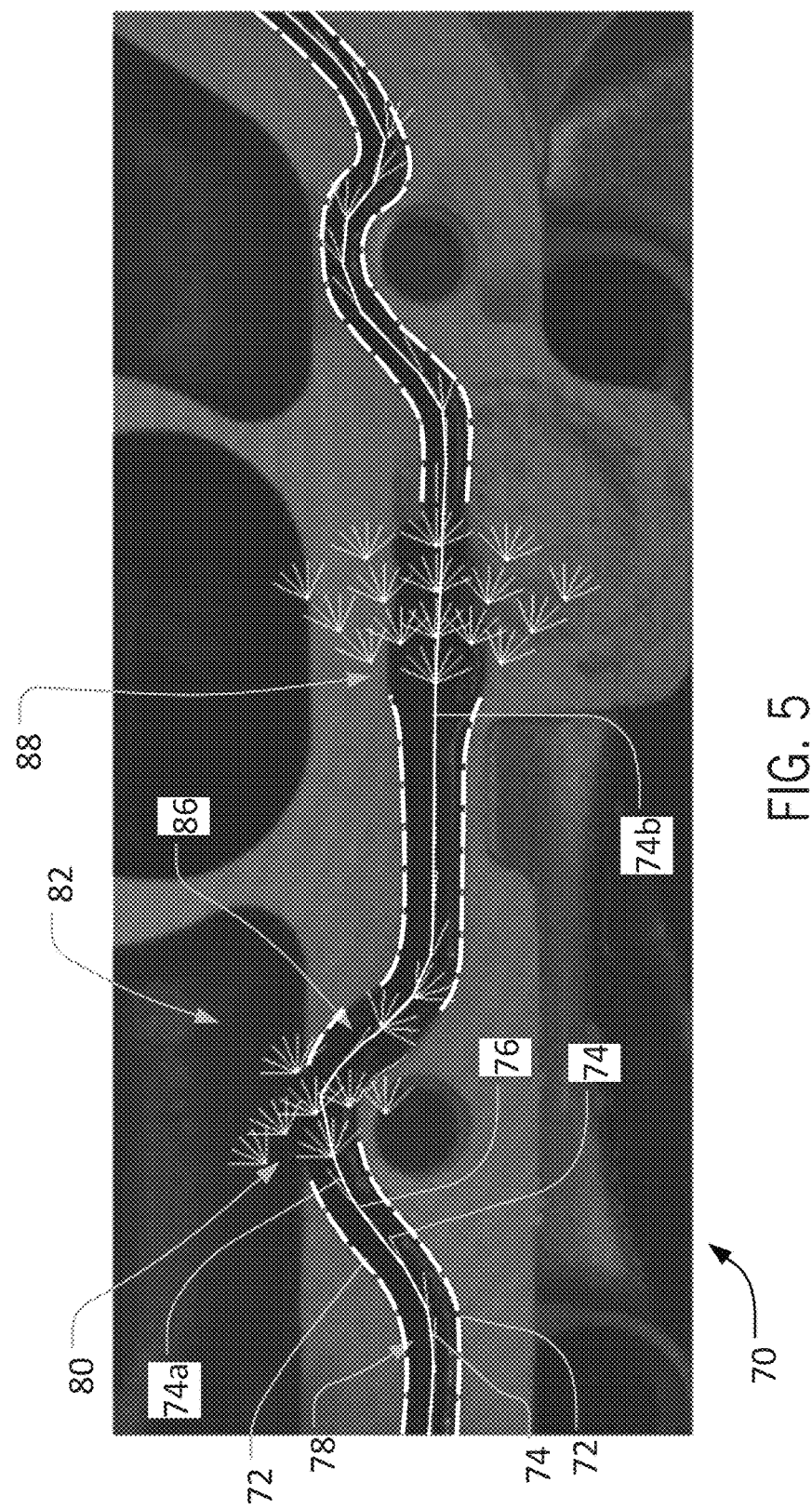
FIG. 5 is a partial schematic view of another training image for bead detection, illustrating analysis of multiple irregular bead portions according to an aspect of the invention.

FIG. 5 illustrates another example of the "skipping" approach discussed above, but with a maximum number of permitted skips (i.e., a maximum "skip count") set to five. For example, on a training image 70, a bead inspection system according to the invention can implement bead analysis as described above, generally identifying bead directions 74 (only some numbered), bead edges 72 (only some numbered), and a bead centerline 76 on a bead 78, as illustrated.

At a first region 80 of the bead 78, due to intersection of the bead 78 with a hole 82 in the underlying part, the bead inspection system may not be able to appropriately characterize the bead 78 (e.g., may be able to identify only a single edge, rather than a set of edge pairs). Accordingly, the bead inspection system can implement a succession of skips, with analysis of each subsequent region starting at an extension of a last known bead direction 74a, and expanding successively farther outwardly from that reference (e.g., in groups of search directions that vary internally by 22.5 degrees and that radiate from points that are aligned along lines that extend at successive angles of 22.5 degrees relative to the direction 74a). After two skips, it can be seen that a first downwardly deviated set 86 of search directions results in successful identification of bead characteristics. Accordingly, the skip count can be reset and analysis can proceed as described above.

Similarly, at a second region 88 of the bead 78, due to unexpected spreading of the bead 78 on the part (or other factors), the bead inspection system may again not be able to appropriately characterize the bead 78. Accordingly, as also described with regard to the region 80, the bead inspection system can implement a succession of skips, with analysis of each subsequent region starting at an extension of a last known bead direction 74b, and expanding successively farther outwardly from that starting point (e.g., in groups of search directions that vary internally by 22.5 degrees and that radiate from points that are aligned along lines that extend at successive angles of 22.5 degrees relative to the direction 74b). In this case, the bead inspection system is not able to successful identify bead characteristics until four skips have been executed. However, because the maximum skip count has been set to five, the analysis is permitted to continue to—and beyond—this point.

As also noted above, in some implementations, analysis of a bead on a training image can proceed from a starting indicator in one direction along the bead. In some such cases, once an end of the bead along the initial direction has been identified, the bead inspection system can return to the starting indicator and proceed with analysis in another (e.g., opposite) direction along the bead.

Figure 6:
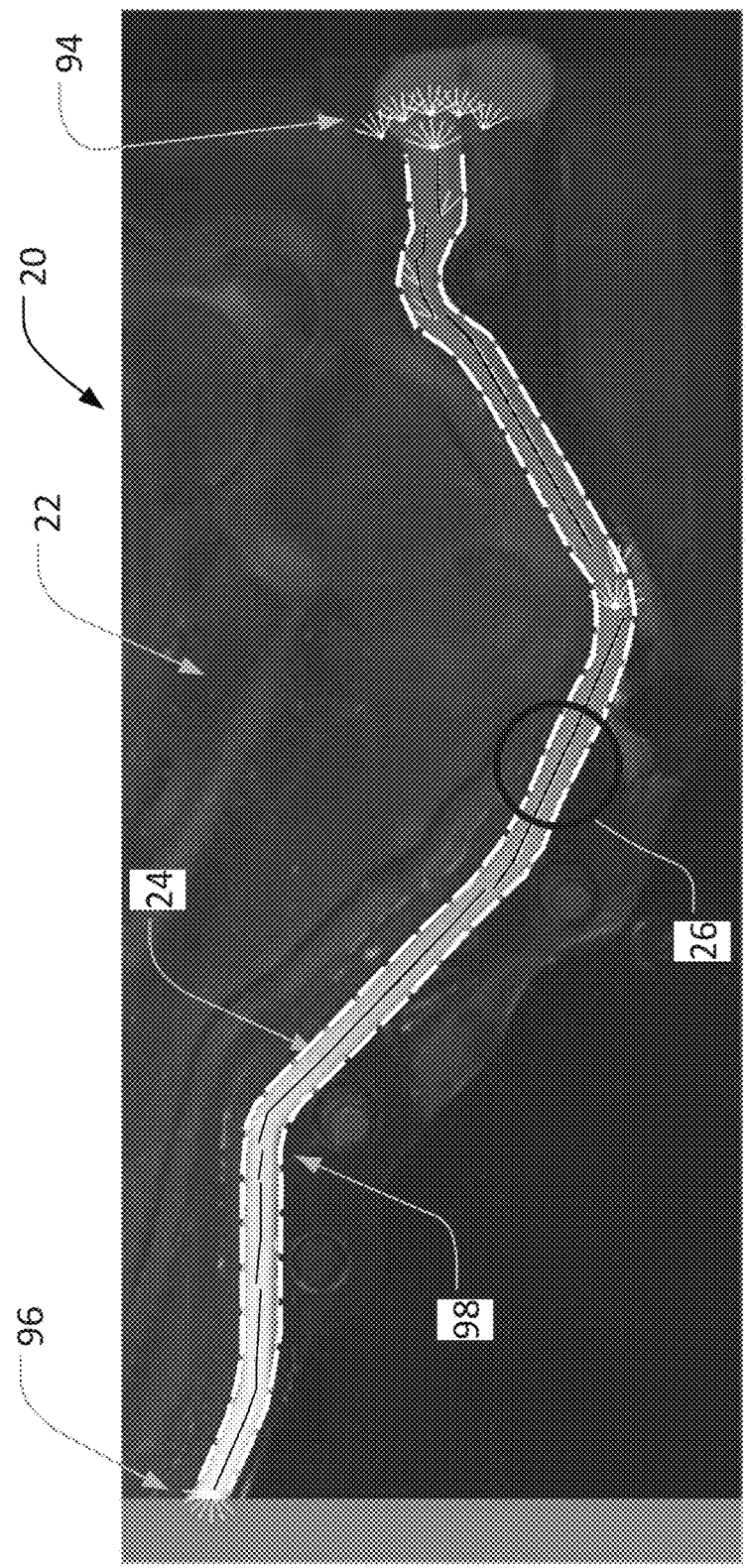
FIG. 6 is a schematic view of the training image of FIG. 1, illustrating a bead profile detected on a particular execution of a training operation according to an aspect of the invention.

In some implementations, a bead inspection system can identify the end in a particular direction based on a failure to identify bead edge pairs, bead direction, or other bead characteristics before the maximum number of "skips" is reached. As illustrated in FIG. 6, for example, with a maximum skip count of 1, analysis of the bead 24 can progress generally to the right from the starting indicator 26, until, in region 94, analysis fails to characterize the bead 24 after executing a single skip. Having thus identified a potential end of the bead 24, the analysis can return to the starting indicator 26 and progress to the left until a left-side end of the bead 24 is identified in a similar manner (e.g., in a region 96). Based on the set of bead directions and edge pairs identified from this analysis, a relatively comprehensive bead profile 98 can accordingly be identified.

Although analysis of the bead with caliper groups is described in the examples above, other approaches are possible. For example, other known techniques for identifying local bead direction (or other characteristics) can be applied with a similarly successive approach as described above, in order to compile a set of directional data for a relevant bead.

Failure to identify bead characteristics with appropriate confidence can result from a variety of factors. For example, in some cases, as illustrated in FIG. 3, poor image quality can sometimes result in locally poor contrast between a bead (e.g., the bead 24) and a background substrate (e.g., the structure 22). Similarly, aspects of a particular structure (e.g., holes or other local formations) adjacent to a bead can also result in poor contrast between a bead and the background.

In some cases, as also discussed below, a user can specify particular properties or guidelines for a training or subsequent bead analysis to address these issues. Similarly, in some cases, an iterative approach to bead analysis during training (e.g., with different parameters for the caliper groups or different anticipated bead characteristics) can result in overall successful bead identification, even if a particular pass along the bead is relatively unsuccessful. For example, a first pass along a bead can use a first set of parameters for caliper groups, such as a first set of settings for the number of calipers per group, the width of each individual caliper, the spacing (e.g., separation or overlap) between adjacent calipers, the various parameters for image (e.g., Gaussian) filters, the parameters for contrast thresholds, the parameters for the extension of the calipers beyond the expected width of the bead, and so on. Subsequent passes along the bead can then use different sets of these or other parameters, in order to maximize the chances of identifying a high-confidence path (or paths) for the bead with at least one of the passes.

In some implementations, relevant analysis parameters (e.g., parameters for caliper groups) can be determined based on default settings. In some implementations, relevant analysis parameters can be determined based on analysis of the relevant bead itself. For example, as well as analyzing a bead in a training image at a relevant starting indicator to identify initial bead characteristics (e.g., edge pairs and bead direction), a system according to the invention can also analyze the bead at the starting indicator to identify appropriate sets of analysis parameters. In some implementations, multiple sets of analysis parameters can be identified (e.g., by default and/or based on analysis at the starting indicator) in order to guide successive analysis passes on the training image.

Generally, a bead profile (e.g., the bead profile 98) identified from a training image by a system according to the invention (e.g., as described above) can include information sufficient to appropriately identify the profile of a bead (e.g., a polyline path) over a relevant region or set of regions (e.g., over the full length of the bead). In some cases, along with the bead profile, a bead inspection system according to the invention can also identify—and associate with an appropriate bead profile—other characteristics of a bead, including color, contrast, width, and so on.

In some cases, a determined bead profile (e.g., the bead profile 98) and associated characteristics (as applicable) can simply be adopted as an expected bead profile (and bead characteristics) for the operation that produced the bead 24. Accordingly, the relevant bead profile, along with expected bead characteristics, as determined, for example, via the analyses described above, can be used in order to inspect subsequently created non-training beads.

Figure 7:
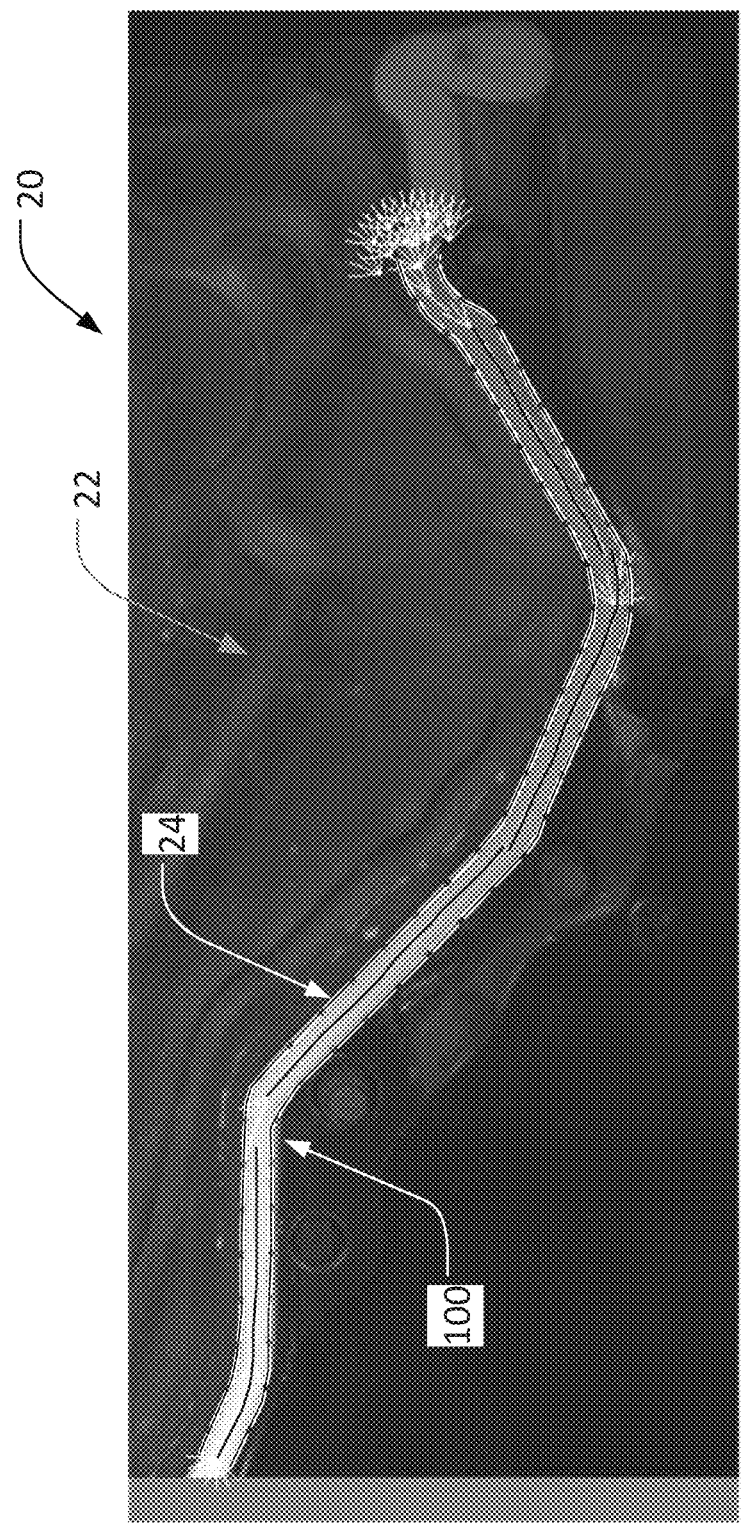
FIG. 7 is a schematic view of the training image of FIG. 1, illustrating a different bead profile detected on a different execution of a training operation according to an aspect of the invention.

In some cases, multiple bead profiles (and, potentially, additional other bead characteristics) can be determined, and then a best profile (and characteristic set) or profiles (and characteristic sets) can be selected to guide subsequent bead inspection. For example, as illustrated in FIG. 7, in addition to the bead profile 98, a bead inspection system can identify an alternative bead profile 100 for the bead 24, based on analysis of the training image 20 using different parameters than were used to determine the bead profile 98. For example, in some embodiments, the bead profile 100 can be determined using different parameters for caliper groups than were used to determine the bead profile 98.

When multiple bead profiles (or other bead data) have been determined, it may sometimes be useful to present the bead profiles (or other bead data) to a user, who can then specify which of the bead profiles best matches the bead profile that has been visually identified by the user. In some cases, multiple profiles can be presented to a user simultaneously (e.g., overlaid with different colors or line types). In some cases, the bead inspection system can score or otherwise rank different bead profiles (or other bead data) and present more highly ranked profiles (or other data) to users first. For example, as illustrated in FIG. 8, the bead profile 98 can be presented to a user first, in a visually simplified format, in order to allow the user to either verify the profile 98 as being an appropriate profile for subsequent bead inspection, or to pass on the profile 98 (at least temporarily) in order to view lower-ranked (or other) profiles.

In some implementations, it may be useful to use multiple training images in order for a bead inspection system to execute training operations (e.g., including the training operations described above). In some implementations, it may be useful to combine training images with and without relevant beads in order to enable more accurate bead analysis. In this regard, for example, training images without beads can be treated as background images to be combined with (e.g., subtracted from) training images with beads, in order to help isolate relevant beads for training analysis. This can be useful, for example, in order to avoid issues that might otherwise arise from the use of images with bright or "hot" spots, from the use of images with lower contrast between beads and background structure, or otherwise.

Figure 10:
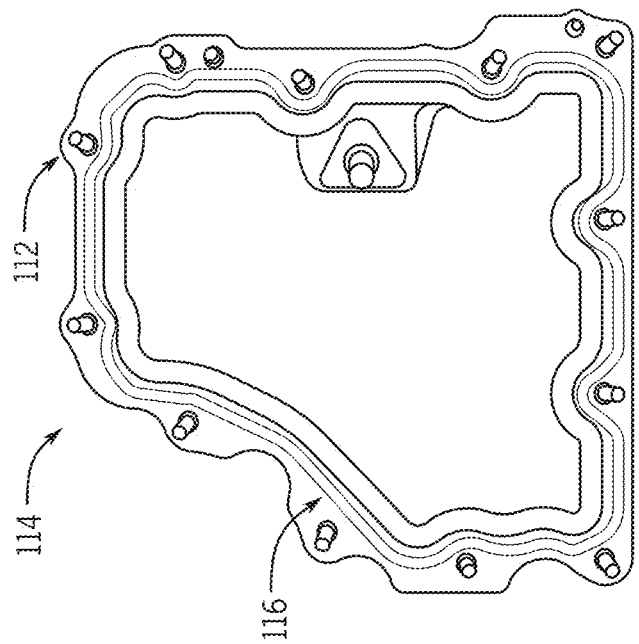
FIG. 10 is a schematic view of a second reference image, with a bead, for use with the first reference image of FIG. 9.
Figure 9:
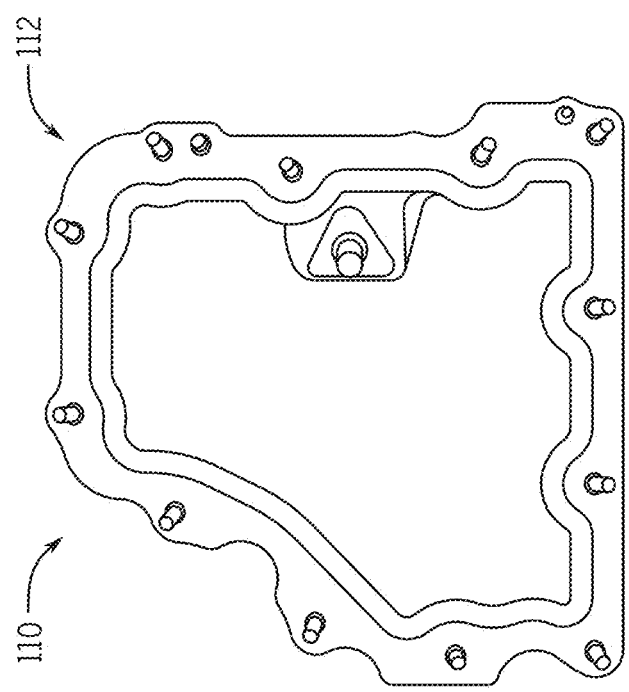
FIG. 9 is a schematic view of a first reference image, without a bead, for use with embodiments of the invention.

In this regard, for example, as illustrated in FIGS. 9 and 10, a first training image 110 can be captured of a part 112 to which a bead will be—but has not yet been—applied. A second training image 114 of the part 112 with a bead 116 can also be captured, with similar perspective, lighting, and other imaging parameters as the image 114, as appropriate. Using known techniques, the bead-less training image 110 can then be subtracted from (or otherwise combined with) the training image 114 in order to generally isolate the bead 116. The isolated bead 116 can then be analyzed by a bead inspection system (e.g., as described above), with generally reduced potential for failed identification of local bead profiles, resulting in a combined training image 118 with a determined bead profile 120, as illustrated in FIG. 11.

As also discussed above, in some cases a bead may interact with a supporting structure in ways that make the bead locally difficult to identify. For example, where a dark-on-light bead passes close to (e.g., immediately adjacent to) a hole in a relevant structure (or other "dark" feature) it may not be possible to use typical techniques (e.g., contrast analysis) to identify the bead—even if a training or inspection image is of relatively high quality. In conventional inspection systems, the presence of these types of regions can result in beads failing inspection not because the beads are inadequate, but simply because the bead cannot be adequately identified in the relevant image.

Figure 12:
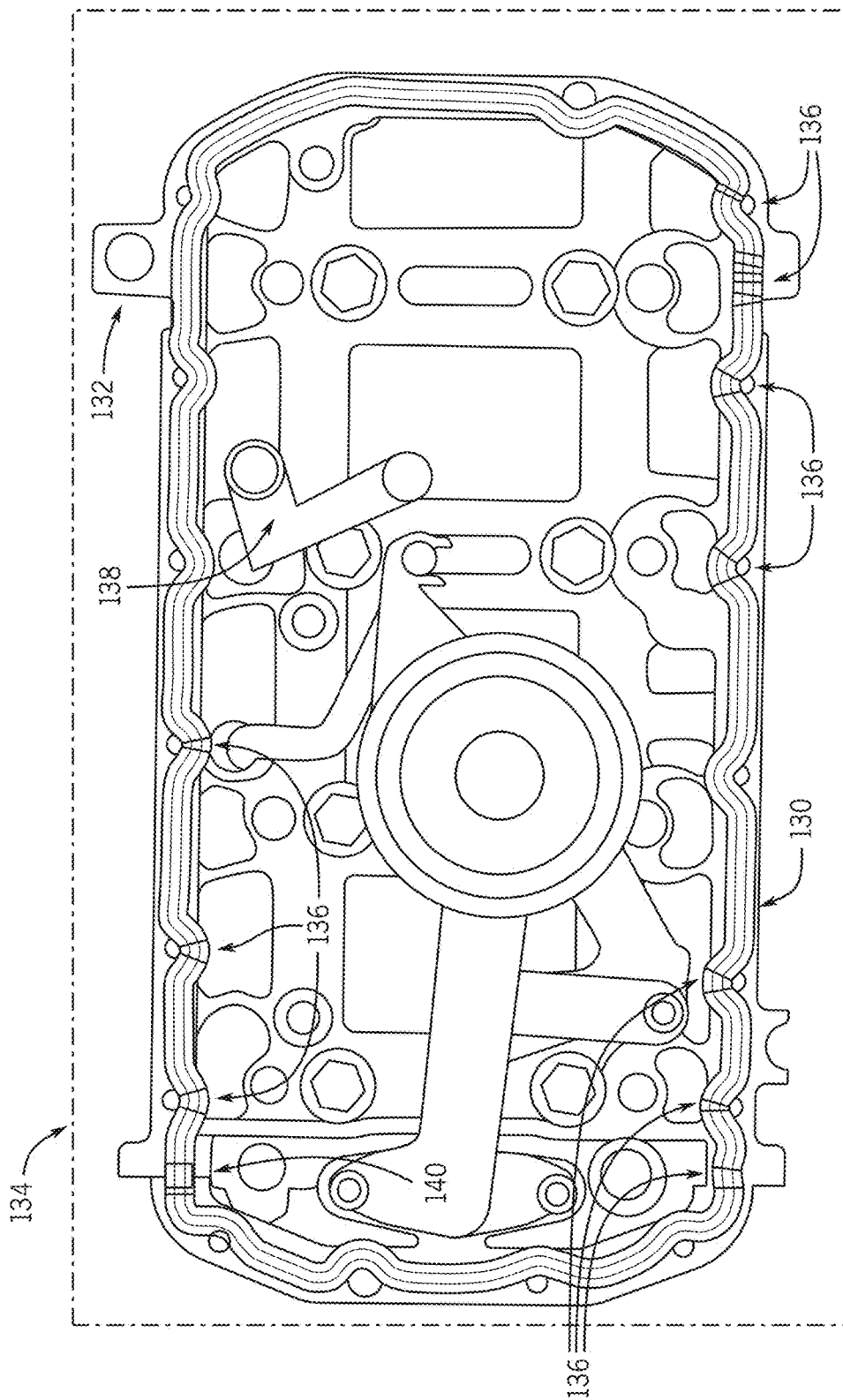
FIG. 12 is a schematic view of a training image illustrating bead detection according to an aspect of the invention.
Figure 13:
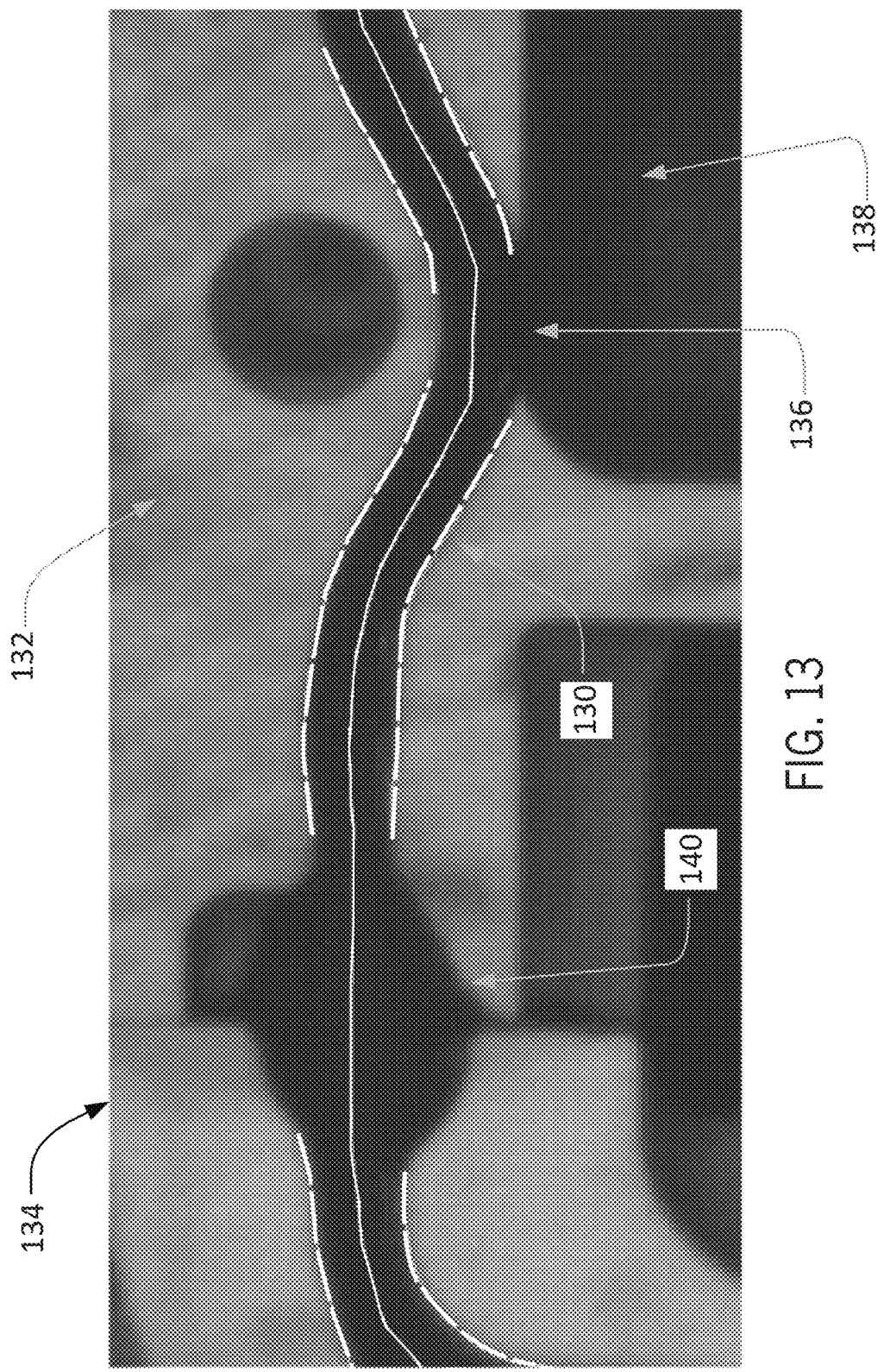
FIG. 13 is an enlarged schematic view of a portion of the training image of FIG. 12.

In this regard, accordingly, some embodiments of the invention can usefully allow a user to disable searching for a bead over select regions (i.e., to selectively "mask" the bead) during bead inspection operations. As illustrated in FIGS. 12 and 13, for example, a training analysis (e.g., similar to that described above) may have identified a bead profile 130, which is represented as superimposed on a part 132 in a training image 134. In certain regions 136 of the training image 134, it can be seen that the bead profile 130 passes so closely to a central opening 138 in the part 132 that contrast-based analysis may not be expected to reliably identify the edges of the bead that border the opening 138. Similarly, over other regions (e.g., a region 140) of the training image 134, it can be seen that characteristics of the bead in the training image (e.g., due to a feature on the part 132 encouraging the bead material to spread) resulted in an inability to reliably identify any edges of the bead.

In some implementations, in order to avoid a bead inspection system failing beads during inspection due to the difficulties noted above (e.g., rather than because a relevant bead is actually of sub-standard quality), a bead inspection system according to the invention can permit a user to designate regions along the bead profile 130 where identification of one or more edges of a bead should not be expected (i.e., to selectively mask the bead profile). For example, a user can click along the regions 136 and 140 to indicate that only a single bead edge should be expected along the regions 136, and that no bead edges should be expected along the region 140. These masking indications can then be incorporated into later bead inspection, so that beads are not necessarily failed due to incomplete (or missing) identification of bead edges at the regions 136 and 140.

Figure 14:
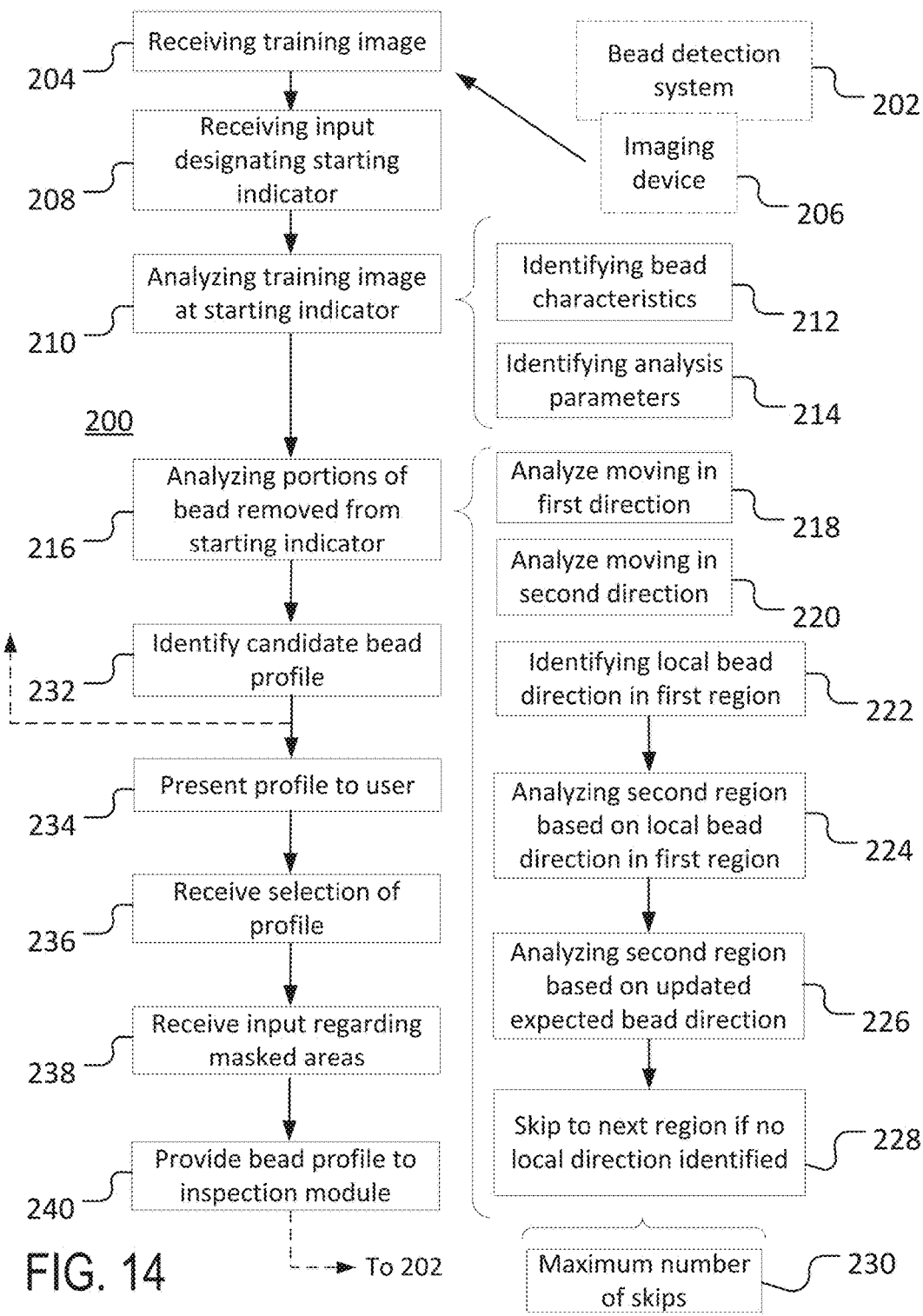
FIG. 14 is a schematic view of a bead detection training method according to an embodiment of the invention.

Consistent with the discussion above, some embodiments of the invention can include computer-implemented methods, including methods executed by software or hardware modules of different machine-vision systems. In some embodiments, a computer-implemented training method can be executed as part of a stand-alone training system for bead detection, or as part of a module (e.g., a discrete or integrated sub-system) of a larger bead detection system. As one example, as illustrated in FIG. 14, an embodiment of the invention can include a training method 200 for use as part of, or to provide inputs to, a bead detection system 202 that includes one or more computing devices (e.g., one or more general or special purpose processor devices).

In some implementations, the method 200 can be used to implement one or more of the operations described above (e.g., with regard to FIGS. 1-13), and/or various other operations. In the illustrated implementation, for example, the training method 200 can include receiving 204 a training image (e.g., from an imaging device 206 included in the bead detection system 202). In some embodiments, the received 204 training image can be an image that includes a bead and that is captured using characteristic imaging parameters for a bead inspection system. In this way, for example, detection of the bead on the training image may reasonably approximate detection of a bead on other images during actual bead inspection.

In some implementations, as illustrated in the example training image 20 of FIG. 1, the received 204 training image can be a single image of a bead and an underlying substrate (e.g., a bead of adhesive or sealant material on a structural part). In some implementations, the received 204 training image can be part of a set of images, such as a set including a reference image without a bead and a corresponding image with a bead, as illustrated with regard to images 110 and 114 in FIGS. 9 and 10. In some implementations, the received 204 training image can be an image resulting from a combination of reference images, such as a subtraction of an image without a bead from an image with a bead, as illustrated in FIG. 11.

Once a training image has been received 204, the method 200 can further include receiving 208 an input (e.g., a user input) that designates a starting indicator for training analysis on a bead in the training image. In some embodiments, a starting indicator designated by the received 208 input can indicate a starting region that surrounds a discrete portion of the bead on the received 204 image. For example, a received 208 input can include a user input that locates (and, in some implementations, provides sizes or other aspects for) a starting indicator, such as the circular starting indicator 26 illustrated in FIG. 1. In some implementations, a starting indicator can be selected (e.g., via user input) to indicate a region of a bead on a training image with visual properties (in the training image) that are relatively characteristic of the bead as a whole.

Once a starting indicator has been designated by the received 208 input, the method 200 can include analyzing 210 the received 204 training image at the starting indicator. For example, the method 200 can include analyzing 210 a portion of the bead and surrounding substrate that is contained within a starting region, such as the region designated by the starting indicator 26 (see FIG. 1).

In some implementations, analyzing 210 the received 204 training image can be implemented in order to identify 212 any number of different bead characteristics. In some implementations, the identified 212 bead characteristics can include bead color (e.g., absolute color values or relative color designators, such as light-on-dark or dark-on-light), local bead width, local bead direction, minimum bead contrast relative to the surrounding substrate, and so on.

In some embodiments, analyzing 210 the received 204 training image at the starting indicator can include identifying 214 other parameters for subsequent analysis of the bead away from the starting indicator (e.g., outside of a relevant starting region). For example, where caliper groups are to be generally used for analysis of the bead in the received 204 training image (see, e.g., FIG. 3), analyzing 210 the training image can include identifying parameters for the caliper groups, including a number of calipers per group, a width of individual calipers, a spacing between adjacent calipers, image filter parameters for caliper analysis (e.g., half Gaussian width values), a contrast threshold, a caliper extension beyond an expected width of the bead, and so on.

In some implementations, following analysis 210 of the received 204 training image at the starting indicator, the method 200 can further include analyzing 216 portions of the bead that are spaced apart from the starting indicator (e.g., portions of the bead that are outside of the starting region corresponding to the starting indicator or otherwise spaced apart from the starting indicator) in order to identify a candidate bead profile. For example, successive, adjacent regions of a bead on a received 204 training image can be analyzed 216 using caliper groups, based on bead characteristics and analysis (e.g., caliper-group) parameters that were identified 212, 214 based on analyzing 210 the training image at the starting indicator.

In some implementations, the bead in the received 204 training image can be first analyzed 218 moving in a first direction away from the starting indicator and then analyzed 220 moving in a second direction away from the starting indicator. For example, as illustrated in FIG. 6, the bead can be analyzed 218 moving along the bead in a first direction until a first end of a candidate bead profile for the bead has been identified, then can be analyzed 22o moving along the bead in a second direction until a second end of the candidate bead profile has been identified. In other implementations, other approaches are possible, including parallel or alternating analysis of the bead on either side of a starting indicator.

In some implementations, as analysis 216 of a bead proceeds from region to region of the bead, a bead direction identified for a first region can be used as an expected bead direction to guide analysis of a second region. For example, a local bead direction for a first region of a bead can be determined based upon analysis 216 that includes locating one or more edge pairs. An expected bead direction for a second region of the bead (e.g., adjacent to the first region) can then be identified 222 based on (e.g., by copying) the local bead direction for the first region, and the bead can be analyzed 224 in the second region based on the identified 222 local bead direction for the first region. As illustrated in FIG. 3, for example, this approach can lead to efficient identification of successive local bead directions, based on an assumption that a bead may tend not to deviate substantially from a local direction over relatively small distances.

In some implementations, analysis 216 of a bead at a second (or other) region may not appropriately characterize the bead (e.g., may not identify edge pairs or a local bead direction) based on a linear extension of a previously identified 222 local bead direction for an adjacent first region. For example, as illustrated in FIG. 3, as the bead 40 changes directions, the bead direction 40b identified by the caliper group 42b may not correspond particularly closely to a bead direction in an adjacent region (e.g., as analyzed by the caliper group 42c). In this circumstance, and others, it may accordingly be useful to analyze 226 the second region of the bead based on one or more updated expected bead directions different from the identified 222 local bead direction in the first region. For example, it may be useful to analyze 226 the second region of the bead based on updated expected bead directions that deviate from the previously identified 222 local bead direction by a predetermined angle (see, e.g., bead directions 40c', 40c'' in FIG. 3).

In some implementations, if analysis of a particular region of a bead does not result in successful identification of a bead direction, the method 200 can include skipping 228 to another (e.g., adjacent) region of the bead in order to continue the analysis 216 of the bead in that region. For example, in some implementations, it may be possible to identify 222 a local bead direction in a first region, but may not be possible to identify a local bead direction in a second region, even after analysis 224, 226 based on the identified 222 local bead direction and an updated expected bead directions. In some cases, it may then be appropriate to skip 228 to a third (e.g., adjacent) region for further analysis 216.

In some implementations, when skipping 228 to subsequent regions of a bead, it may be useful to implement analysis similar to that described above—e.g., to also analyze 224 the subsequent (e.g., third, fourth, and so on) region based on a previously identified 222 local bead direction. As illustrated in FIG. 5, for example, analysis 216 of the region 88 of the bead 78 can proceed in a successively expanding manner, based on an initially identified 222 local bead direction and predetermined angular deviations therefrom, until a new local bead direction is successfully identified.

In some implementations, the method 200 may limit the number of skips 228 to a predetermined maximum number 230 of skips. In some implementations, as illustrated relative to the region 94 and the bead profile 98 in FIG. 6, an end of a candidate bead profile can be identified 232 based upon analysis 216 of the relevant bead reaching the maximum number 230 of skips without successfully identifying a local bead direction (or other bead characteristic).

In some implementations, methods according to the invention can be implemented somewhat iteratively. This may be useful, for example, in order to identify multiple candidate bead profiles, from which a particular candidate (or candidates) can be selected for use during actual bead inspection. As illustrated in FIG. 14, for example, based on an initial analysis 216 of the bead, a first candidate bead profile can be identified 232. As appropriate, aspects of the method 200 can then be repeated, in order to identify 232 one or more additional candidate bead profiles. For example, a first analysis 216 of the bead can be executed based on a first set of identified 214 analysis parameters (e.g., a first set of caliper group parameters), then a second analysis 216 of the bead can be executed based on a second set of identified 214 analysis parameters (e.g., a second set of caliper group parameters).

Where multiple candidate bead profiles have been identified 232, the method 200 may sometimes include presenting 234 the identified 232 candidate profiles to a user and receiving 236 a selection of one or more of the identified 232 profiles for use during actual bead inspection (or other operations).

In some implementations, the method 200 may include receiving other user input. For example, the method 200 can sometimes include receiving 238 input from a user regarding areas of an identified 232 candidate bead profile that should be masked (i.e., that should not be used to evaluate beads during actual bead inspection). As illustrated in FIGS. 12 and 13, for example, this may be useful in order to ensure that areas of a bead that may not particularly susceptible to reliable image-based analysis 216 do not result in excessive improper failure of beads during actual inspection.

Once one or more appropriate bead profiles have been identified 232 and, as appropriate, selected and/or masked via received 236, 238 user input (or otherwise), the method 200 can include providing 240 the relevant bead profile(s) to an inspection module (e.g., part of the bead detection system 202) for use during actual bead inspection. In some implementations, for example, a bead profile determined with the method 200 can be provided 240 to the bead detection system 202 for use during actual (e.g., real-time) bead inspection.

It should be noted that the spatial arrangement of operations as illustrated in FIG. 14 can, but does not necessarily, correlate with the temporal order of corresponding operations during implementation of the method 200. Further, in some implementations, different operations, including those that are expressly described sequentially herein, can be executed in parallel. Further, connections between operations as illustrated in FIG. 14 (e.g., as may indicate flow of data between software or hardware modules or an ordering of particular operations) are provided by way of example only. In some implementations, the various illustrated operations and modules (or others) can be interconnected and can otherwise interoperate with each other and/or with operations or modules of additional systems or methods.

In different implementations, different types of imaging devices can be used, including with regard to the imaging device 206 of FIG. 14, or others. Generally, it may be useful to employ one or more of various kinds of 2-D imaging devices (e.g., 2-D cameras) of various configurations, such as area scan cameras or line scan cameras configured, as appropriate, to capture relevant images.

In some implementations, the same imaging device can be used to capture a training image for a part or system, and to capture later inspection images for the same part or system. In some implementations, different imaging devices can be used. For example, a first imaging device (e.g., a first area scan camera) can be used to capture a training image (e.g., for use in the method 200 of FIG. 14), and a second imaging device (e.g., a second area scan camera) can be used to capture inspection images, which may be then be analyzed based on a preceding processing of the training image (e.g., under the method 200 of FIG. 14).

Figure 15:
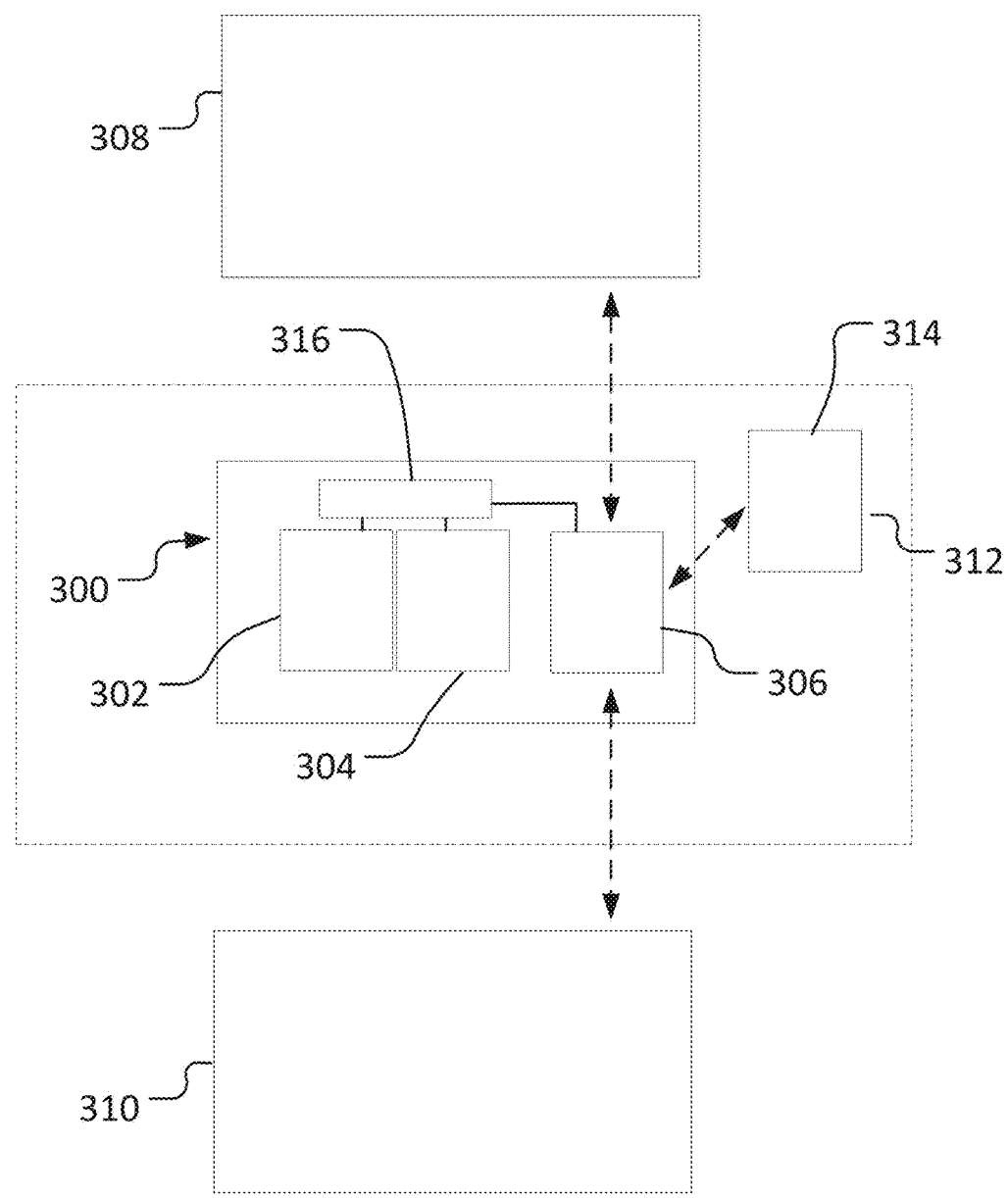
FIG. 15 is a schematic view of machine vision system according to an embodiment of the invention.

Generally, as illustrated in FIG. 15, an imaging device 300 according to one embodiment of the invention (e.g., for use as the imaging device 206 of FIG. 14) can include a lens 302 and an imager 304 (e.g., a CCD or CMOS sensor). In some embodiments, the imaging device 300 can include a communication module 306 (e.g., a wired or wireless communication module) for communication of information to (or from) the imaging device 300 from (or to) a separate device or system, such as a separate computing device or system, a user interface, and so on. For example, in some implementations, imaging (or other) parameters for the imaging device 300 can be selected by a user at a separate computing system 308 with a user interface (not shown), and then transmitted to the imaging device 300. Similarly, imaging data acquired and/or processed by the imaging device 300 can be transmitted from the imaging device 300 to the computing system 308 or to other systems (e.g., an image processing system 310).

In some implementations, the imaging device 300 can be included as part of a larger machine vision system 312 with one or more processor devices 314 that may be separate from the imaging device 300. In some implementations, the imaging device 300 can transmit acquired image data to the machine vision system 312, the separate image processing system 310, the separate computing system 308, or other systems for processing.

In some implementations, the imaging device 300 can itself include one or more processor devices 316, which can be used, for example, to process imaging data acquired by the imaging device 300 before the data is transmitted (e.g., via the communication module 306) to another module or system, or to implement other functionality. For example, the one or more processor devices 316 (or other processor devices) can implement one or more operations of the method 200 of FIG. 14 with regard to training image acquired by the imaging device 300.

While the invention has been described with reference to example embodiments, it will be understood by those skilled in the art that various changes may be made and equivalents may be substituted for elements thereof without departing from the scope of the invention. In addition, many modifications will be appreciated by those skilled in the art to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A training method for a bead detection system, for use with a training image that includes a representation of a bead on a substrate, the training method comprising:
receiving, with one or more computing devices, an input designating a starting indicator that corresponds to a discrete portion of the bead on the training image;
analyzing, with the one or more computing devices, the training image at the starting indicator to identify one or more characteristics of the bead;
analyzing, with the one or more computing devices and based on the one or more characteristics of the bead, one or more portions of the bead that are spaced apart from the starting indicator to identify a candidate bead profile; and
providing, with the one or more computing devices, the candidate bead profile to an inspection module for subsequent inspection of beads in non-training images.

2. The training method of claim 1, wherein the starting indicator includes an indicator shape that surrounds the discrete portion of the bead on the training image.

3. The training method of claim 2, wherein substantially all of the bead on the training image is located outside the indicator shape.

4. The training method of claim 1, wherein analyzing the one or more portions of the bead to identify a candidate bead profile includes:
identifying an expected bead direction based on a prior analysis of a first region of the bead;
analyzing a second region of the bead, adjacent to the first region, based on the expected bead direction, to identify a local bead direction at the second region of the bead; and
if the local bead direction at the second region of the bead is not found to correspond to the expected bead direction, analyzing the second region of the bead based on one or more updated expected bead directions that deviate from the expected bead direction by a predetermined angle.

5. The training method of claim 4, wherein analyzing the one or more portions of the bead to identify the candidate bead profile includes skipping to a third region adjacent to the second region if attempts to identify the local bead direction at the second region are unsuccessful.

6. The training method of claim 5, wherein a number of skips to adjacent portions of the bead based on unsuccessful attempts to identify local bead directions is limited by a predetermined maximum number of skips.

7. The training method of claim 6, wherein an end of the candidate bead profile is identified based upon reaching the predetermined maximum number of skips.

8. The training method of claim 1, wherein analyzing the one or more portions of the bead to identify the candidate bead profile includes:
analyzing the bead along a first direction away from the starting indicator until a first end of the candidate bead profile is identified; and
after identifying the first end of the candidate bead profile, analyzing the bead along a second direction away from the starting indicator until a second end of the candidate bead profile is identified.

9. The training method of claim 1, wherein the candidate bead profile is a first candidate bead profile;
wherein the one or more portions of the bead are analyzed to identify the first candidate bead profile using a first set of analysis parameters; and
wherein the training method further includes analyzing the one or more portions of the bead to identify a second candidate bead profile based upon the one or more characteristics of the bead and a second set of analysis parameters that are different from the first set of analysis parameters.

10. The training method of claim 9, further comprising: presenting the first and second candidate bead profiles to a user for selection of one of the first and second candidate bead profiles to be provided to the inspection module.

11. The training method of claim 9, wherein the first and second sets of analysis parameters include parameters for caliper groups for analysis of the one or more portions of the bead.

12. The training method of claim 11, wherein the parameters for the caliper groups include one or more of: a number of calipers per group, a width of individual calipers, a spacing between adjacent calipers, image filter parameters, a contrast threshold, and a caliper extension beyond an expected width of the bead.

13. The training method of claim 12, wherein the parameters for the caliper groups are determined based on analysis of the bead at the starting indicator.

14. The training method of claim 1, further comprising: receiving a user input designating one or more regions on the candidate bead profile for masking during the subsequent inspection of beads.

15. The training method of claim 1, wherein the one or more characteristics of the bead include at least one of: bead color, local bead width, local bead direction, and minimum bead contrast.

16. A training method for a bead detection system, for use with a training image that includes a representation of a bead on a structure, the training method comprising:
   identifying, with one or more computing devices, a starting region on the bead on the training image based upon a user-designated starting indicator;
   analyzing the bead within the starting region, with the one or more computing devices, to identify one or more characteristics of the bead;
   analyzing the bead outside of the starting region, with the one or more computing devices and based on first analysis parameters and the one or more characteristics of the bead, to identify a first candidate bead profile;
   analyzing the bead outside of the starting indicator, with the one or more computing devices and based on the one or more characteristics of the bead and second analysis parameters that are different from the first analysis parameters, to identify a second candidate bead profile;
   determining, with the one or more computing devices, an inspection bead profile based on at least one of the first candidate bead profile and the second candidate bead profile; and
   providing, with the one or more computing devices, the inspection bead profile to an inspection module for subsequent inspection of beads in non-training images.

17. The training method of claim 16, wherein analyzing the bead outside of the starting indicator further includes:
   identifying an expected bead direction based on a prior analysis of a first region of the bead;
   analyzing a second region of the bead, adjacent to the first region, based on the expected bead direction, to identify a local bead direction at the second region of the bead; and
   if the local bead direction at the second region of the bead is not successfully identified based on the expected bead direction, analyzing the second region of the bead based on one or more updated expected bead directions that deviate from the expected bead direction by a predetermined angle.

18. The training method of claim 17, wherein analyzing the bead outside of the starting region further includes:
   if the local bead direction at the second region of the bead is not successfully identified based on the one or more updated expected bead directions, analyzing a third region of the bead adjacent to the second region, based on the expected bead direction.

19. The training method of claim 18, wherein analyzing the bead outside of the starting region further includes:
   if the local bead direction at the third region of the bead is not successfully identified based on the expected bead direction, analyzing the third region of the bead based on an additional one or more updated expected bead directions that angularly deviate from the expected bead direction by the predetermined angle, as measured from the first region of the bead.

20. A bead recognition training system comprising:
   an imaging device configured to capture a training image of a bead; and
   a processor device and a memory configured to store executable software, wherein the executable software includes instructions, executable by the processor, for:
      receiving the training image;
      receiving a user input that provides a starting indicator designating a discrete portion of the bead on the training image, with substantially all of the bead on the training image being located outside of the discrete portion;
      analyzing the bead within the discrete portion of the bead to identify one or more characteristics of the bead;
      analyzing the bead outside of the discrete portion of the bead, based on the identified one or more characteristics of the bead, to determine one or more candidate bead profiles; and
      providing at least one of the candidate bead profiles to an inspection module for subsequent inspection of beads in non-training images.

* * * * *